(12) United States Patent  
Miller et al.

(10) Patent No.: US 7,856,933 B2
(45) Date of Patent: Dec. 28, 2010

(54) WOODEN DOWEL IN PALLET ASSEMBLY

(75) Inventors: Michael Miller, Winnetka, IL (US); Andrew P. Studdert, Wilmette, IL (US); Daniel Tingley, Norfolk, VA (US)

(73) Assignee: Miller Dowel Company, Northfield, IL (US)

( * ) Notice: Subject to any disclaimer, the term of this patent is extended or adjusted under 35 U.S.C. 154(b) by 402 days.

(21) Appl. No.: 11/982,596

(22) Filed: Nov. 2, 2007

(65) Prior Publication Data

US 2008/0115699 A1    May 22, 2008

Related U.S. Application Data

(63) Continuation-in-part of application No. 10/939,933, filed on Sep. 13, 2004, now abandoned.

(51) Int. Cl.
*B65D 19/00* (2006.01)
*B65D 19/31* (2006.01)

(52) U.S. Cl. .................. 108/56.1; 108/51.11

(58) Field of Classification Search ............. 108/56.1, 108/51.11, 57.17, 57.14
See application file for complete search history.

(56) References Cited

U.S. PATENT DOCUMENTS

| | | | |
|---|---|---|---|
| 100,055 A | 2/1870 | Montgomery | |
| 332,308 A | 12/1885 | Valentine | |
| 569,235 A | * 10/1896 | Rockwell | 403/265 |
| 876,985 A | 1/1908 | Malancon | |
| RE13,915 E | 5/1915 | Evans | |
| 1,229,565 A | 6/1917 | Ahlgren | |
| 2,621,006 A | 12/1952 | Norrefeldt et al. | |
| 2,667,795 A | 2/1954 | Bowen | |
| 2,817,620 A | 12/1957 | Golick et al. | |
| 3,016,222 A | 1/1962 | Arthur | |
| 3,104,430 A | 9/1963 | Badali | |
| 3,153,283 A | 10/1964 | Weissman | |
| 3,204,583 A | 9/1965 | Nicholson | |
| 3,221,458 A | 12/1965 | Lucas | |
| 3,527,486 A | 9/1970 | Gamp | |

(Continued)

FOREIGN PATENT DOCUMENTS

CA    465953    6/1950

(Continued)

OTHER PUBLICATIONS

International Search Report regarding PCT/US2008/081077, Dec. 29, 2008.

(Continued)

*Primary Examiner*—Darnell M Jayne
*Assistant Examiner*—Timothy M Ayres
(74) *Attorney, Agent, or Firm*—Husch Blackwell Welsh Katz

(57) ABSTRACT

An improved pallet that is capable of easy assembly, functionally adequate for some situations and capable of easy disassembly. In one form of the invention, a pallet is provided that is made of all wood. In one embodiment, the pallet may be comprised of a plurality of stringers with bores, a plurality of deck boards with openings, and a plurality of wooden dowels disposed in the bores and openings to connect the stringers and deck boards.

22 Claims, 6 Drawing Sheets

U.S. PATENT DOCUMENTS

| | | | |
|---|---|---|---|
| 3,575,520 | A | 4/1971 | Halpern |
| 3,635,573 | A | 1/1972 | Halpern |
| 3,756,635 | A | 9/1973 | Beers |
| 3,850,054 | A | 11/1974 | Weissman |
| 3,883,258 | A | 5/1975 | Hewson |
| 4,128,356 | A | 12/1978 | Carlisle |
| 4,137,115 | A * | 1/1979 | Lambert .................... 156/257 |
| 4,340,327 | A | 7/1982 | Martins |
| 4,424,753 | A | 1/1984 | Eatherton |
| 4,518,291 | A | 5/1985 | Lang et al. |
| 4,536,044 | A | 8/1985 | Ziegelheim et al. |
| 4,639,197 | A | 1/1987 | Tomare et al. |
| 4,793,745 | A | 12/1988 | Ashbaugh et al. |
| 4,815,902 | A | 3/1989 | Durfee, Jr. |
| 4,884,571 | A | 12/1989 | Baker |
| 5,100,162 | A | 3/1992 | Lo |
| 5,131,783 | A | 7/1992 | Astl |
| 5,232,302 | A | 8/1993 | Wagner et al. |
| 5,265,988 | A | 11/1993 | Schmigalla et al. |
| 5,326,196 | A | 7/1994 | Noll |
| 5,333,555 | A | 8/1994 | McPhee |
| 5,458,069 | A | 10/1995 | Stolzman |
| 5,529,424 | A | 6/1996 | Neubert et al. |
| D371,302 | S | 7/1996 | Spirer |
| 5,584,951 | A | 12/1996 | MacFarland |
| 5,673,629 | A | 10/1997 | Ginnow |
| 5,685,234 | A | 11/1997 | Grigsby et al. |
| 5,768,845 | A | 6/1998 | Beaulieu et al. |
| 5,771,650 | A | 6/1998 | Williams et al. |
| 5,807,015 | A | 9/1998 | Goto |
| 5,960,721 | A | 10/1999 | Huetteman |
| 5,967,056 | A | 10/1999 | Plante |
| D426,766 | S | 6/2000 | Burchall et al. |
| 6,267,527 | B1 | 7/2001 | Miller |
| D456,700 | S | 5/2002 | Miller et al. |
| D484,781 | S | 1/2004 | Miller |
| 6,814,287 | B1 | 11/2004 | Chang et al. |
| 6,871,681 | B2 | 3/2005 | Miller |
| 2003/0089771 | A1 | 5/2003 | Cybulski et al. |
| 2004/0099339 | A1 | 5/2004 | Miller |
| 2006/0054064 | A1 | 3/2006 | Miller et al. |
| 2008/0115699 | A1 | 5/2008 | Miller et al. |
| 2009/0255605 | A1 | 10/2009 | Filion et al. |

FOREIGN PATENT DOCUMENTS

| | | | |
|---|---|---|---|
| CH | 663 0269 | A5 | 11/1987 |
| DE | 1 947 456 | | 9/1970 |
| DE | 3820351 | A1 | 12/1989 |
| FR | 663 069 | | 8/1929 |
| FR | 1.064.660 | | 5/1954 |
| FR | 2 301 441 | | 10/1976 |
| FR | 2 808 779 | A3 | 11/2001 |
| GB | 11581 | | 8/1887 |
| GB | 221280 | | 9/1924 |
| IT | 475429 | | 10/1952 |
| JP | 57126325 | | 8/1982 |
| JP | 63166925 | | 10/1988 |
| JP | 219735 | | 2/1990 |
| JP | 2002-302120 | A | 10/2002 |
| JP | 2002-332041 | A | 11/2002 |
| KR | 100301374 | B1 | 6/2001 |
| KR | 200337382 | Y1 | 12/2003 |
| KR | 200359774 | Y1 | 8/2004 |
| KR | 100578694 | | 8/2005 |
| KR | 100778075 | B1 | 4/2007 |
| WO | WO 91/04196 | A1 | 4/1991 |
| WO | WO 2007/043995 | A1 | 4/2007 |

OTHER PUBLICATIONS

PCT—International Preliminary Report on Patentability from related PCT application, Apr. 9, 2008.
White: "How to Improve the Value of Wood Pallets" (http://www.nwpca.com/IndustryStabdardsSpecifications/HowToImproveTheValue.htm), downloaded Feb. 15, 2004 (3 pages).
Curtis "Treenails", 1918 (http://pc-78-120.udac.se:8001/WWW/Nautica/Shipbuilding/Fastening/Curtis(1918).html) downloaded Oct. 24, 2002.
Mitchell et al,: "Performance tests of Modern Adhesives for Gluing Pallet Deckboard/Stringer Connections", Revised Jul. 15, 1998 (17 pages).
Industrial Fastener Institute "Fastener Standards" $5^{th}$ Edition © 1970 p. L-12 (1 page).
"An Introduction to Wood Pallets" National Wooden Pallet and Container Association. (5 pages), Sep. 13, 2004.
"Wal-Mart Tests RFID with Eight Suppliers", Informationweek.com, May 3, 2004 ((1 page).
"Paxar Unveils New RFID Label Printer", RFID Journal, downloaded Aug. 30, 2004 (2 pages).
Oy, Raja Lava: "Ecopallet 100% Wood, No Nails, Glue or Additives" (2 pages), Sep. 13, 2004.
One page from http://www.millerdowel.com—Welcome page re Miller Dowel Introduces Mini-X (downloaded Jun. 30, 2004).
One page from http://www.millerdowel.com re: Advantages (downloaded Jun. 30, 2004).
Two pages from http://www.millerdowel.com—Using the Miller Dowel (downloaded Jun. 30, 2004).
Three pages from http://www.millerdowel.com—Applications (downloaded Jun. 30, 2004).
Two pages from http://www.millerdowel.com re Kids' Chair Plan (undated).
Five pages from http://web.archive.org/web/20030425203631/http://millerdowel.com, Apr. 25, 2003.
One page prepared by Miller Dowel re Introducing a More Durable, Safer, All-Wood Pallet Fastener from the Miller Dowel Company (undated).
"Standard Test Methods for Pallets and Related Structures Employed in Materials Handling and Shipping", ASTM International, (Reapproved 2003).
Rupert et al.: "Preliminary Performance Evaluation of 48×40, Non-reversible, Partial 4-way, Three Stringer Green Hardwood Pallets Assembled Using Miller Wood Dowel Fasteners", Aug. 28, 2002 (15 pages).
Rupert et al.: "Preliminary Performance Evaluation of 48×40, Non-reversible, Full 4-way, Nine Block Softwood Pallets Assembled Using Miller Wood Dowel Fasteners", Aug. 9, 2006 (11 pages).
Tingley: Wood Dowel—All Glued—Bison Pallet Testing Report (21 pages), May 9, 20j07.
"Uniform Standard for Wood Pallets" Approved Standard for Repair of Wood Pallets included, National Wooden Pallet and Container Association. (www.palletcentral.com) (2 pages), Feb. 6, 2008.
New Pallet Specifications (http://www.nwpca.com/IndustryStandardsSpecifications/2800specs.htm?page-2800 specs...) dated Jan. 27, 2006 (1 page).
Guide to the Pallet Design System (PDS) Pallet Structural Analysis) National Wooden Pallet and Container Association (www.palletcentral.com), Feb. 6, 2008.
Tingley: "ASTM-1185-98a Pallet Test Report for Glued-in-Place Ipe Wood Dowels and Oak Pallets", Sep. 16, 2005 (10 pages).

* cited by examiner

WOODEN DOWEL IN PALLET ASSEMBLY

This application is a continuation in part application of U.S. patent application Ser. No. 10/939,933, filed Sep. 13, 2004 now abandoned.

FIELD OF THE INVENTION

The present invention relates generally to pallets, and more particularly to a pallet having deck boards connected to stringers with wooden dowels having stepped diameter peripheral surfaces which act as internal clamps.

BACKGROUND OF THE INVENTION

Pallets of various types are known in the art. Typical pallets are constructed of wood and include parallel stringers to which transverse deck boards are then nailed or otherwise secured with metal fastener devices to form the pallet. Pallets need to have sufficient strength to withstand the weight of objects loaded thereon and other impact forces to which the pallets are subjected when objects are loaded onto them and when the pallets are moved, as by a fork-lift truck or the like.

In many pallets, pallets are damaged at their lead boards. As a fork lift or other mechanism is brought to engage a pallet, it will often impact the lead board of the pallet with significant force. This shearing force may disengage the lead board or otherwise damage it, yielding a worn or damaged pallet that may not work as well and may be dangerous to users and merchandise.

Also, as pallets are used, they can become worn and weakened, causing some of the stringers or deck boards to break or become at least partially detached, rendering the pallet inoperable or in a dangerous condition. The use of nails or other metal fastener devices can also render pallets dangerous. Many times, the damage to a pallet occurs where the metal nail goes into the wood. The use of metal fasteners can cause checking in the stringers or deck boards. Further faults include product damage or personal injury caused by exposed fasteners and inadequate joint stiffeners.

In an effort to save money and resources, the undamaged portions of worn or damaged pallets are often salvaged and reused in making recycled pallets, used as fuel or sawdust, or put to other uses. Those in the art have employed many methods in their attempts to salvage worn-out pallets by stripping or otherwise disassembling the stringers and deck boards from each other. However, many of these methods require costly machinery or a great deal of time and effort and put workers at significant safety risk. Nails and other metallic fasteners are often a great hindrance in efforts to disassemble pallets. The presence of, for example, nails prevents the use of standard saws or similar devices, which do not effectively cut through nails. Devices that are able to disassemble worn-out pallets that include nails face other disadvantages. First, they are often large, unwieldy and expensive. Second, often times the nails remain in the stringers or deck boards after disassembly. In order to reuse the boards in optimal condition, the nails need be removed, requiring additional time with attendant increased cost and expense.

More recently, companies who utilize pallets have turned to Radio Frequency Identification ("RFID") technology to monitor and track pallet location and other information. To use such technology, encoded RFID tags or devices are placed on a pallet. As the pallet moves through distribution channels, RFID readers scan the devices. By, for example, placing a RFID reader at a dock door of a warehouse, a supplier and customer know when a pallet arrives. Wal-Mart has imposed RFID deadlines on its major suppliers. However, there have been problems implementing RFID systems. One problem that faces RFID technology is the ability to read metal products because metal can prevent RFID readers from operating properly. A pallet without metallic fasteners would thus be desired. Further, liquid inside of objects can absorb RF signals, making reading more difficult. It is thus desirable to have a wooden pallet that can be constructed with drier wood. However, nails and other metallic fasteners often cannot be used to construct a pallet with dry wood because they will cause checking and damage to the wood during construction.

In response to these problems, construction of pallets without utilizing metallic fasteners has been attempted. One such method uses only adhesives to connect stringers to deck boards. However, there are numerous disadvantages to such a pallet. One is that the connection is often times not strong enough to resist typical shearing or other forces. A second disadvantage to such a pallet is the required use of external clamps or similar devices to hold the pieces together while the glue sets. A third disadvantage of this technique is the waste of time between initial alignment and ultimate formation of the pallet. This waste of time stems from the requirement of waiting for the glue to set before use of the pallet. There thus exists a need for a pallet that can be readily and economically assembled, can withstand substantial impact and load forces, can be easily disassembled, including with dry wood, and will not interfere with RF signals or prevent RFID readers from operating properly.

SUMMARY OF THE INVENTION

In carrying out one embodiment of the invention, a pallet made predominately of wood comprises a plurality of wooden stringers. Each wooden stringer comprises four elongated longitudinal surfaces and two end surfaces. A selected longitudinal surface is designated as a mounting surface and has a plurality of bores formed therein so that the longitudinal axes of the bores are generally normal to the mounting surface. The size and shape of the bores can range from a depth completely through the stringer to a smaller depth sufficient to receive a portion of a dowel.

The deck boards can be connected to the stringers by a plurality of wooden dowels. Each of the dowels preferably has a first and second portion. The dowel comprises at least two contiguous dowel sections having different cross-sectional size. The dowels are preferably constructed so that one portion fits into one of the bores in the stringer while the other portion fits into one of the openings in the deck board, thereby connecting the stringer to the deck board. Adhesive is used to augment that connection. The second end of the deck board can be similarly connected to a second stringer so that the deck board is transverse the wooden stringers. A pallet can be formed by so connecting a plurality of deck boards to the stringers.

One benefit of the present invention is to provide a pallet that can be easily assembled through the use of wooden dowels that facilitate attachment of transverse deck boards to parallel stringers in a quick and efficient manner.

Another benefit of the present invention is to provide a pallet of the aforedescribed type that may in one embodiment employ an adhesive in conjunction with the dowels, the dowels being configured to eliminate the need for external clamps to hold the parts together while the adhesive sets or cures. Thus, there is no time wasted after initial alignment and connection because the dowels provide sufficient connectivity to allow for immediate handling and use of the formed pallets.

Another benefit of the present invention is to provide a pallet that works properly. The dowels provide for a connection that is sufficiently strong to resist standard shear and other forces.

Another benefit of the present invention is to provide a pallet that can be more easily disassembled. In the preferred embodiment the dowels are made of wood; therefore, the pallet can be more readily stripped or broken down using standard wood-cutting saws. This allows for an increased number of customers for used or worn pallets, because those customers have no need for specialty equipment to grind up nails.

Another benefit of the present invention is to provide a pallet which can be a carrier of RFID technology. Because the preferred embodiment does not have metal, the pallet will not prevent RFID readers from working properly. The pallet claimed herein can have a RFID device placed on it, and it will be able to be read by RFID readers without fear of a nail or other metal fastener preventing the RFID reader from working properly.

BRIEF DESCRIPTION OF THE DRAWINGS

The features of the present invention which are believed to be novel are set forth with particularity in the appended claims. The drawings may not be to scale. The invention may best be understood by reference to the following description taken in conjunction with the accompanying drawings, in the several figures of which like reference numerals identify like elements, and in which:

DETAILED DESCRIPTION

Figure 1:
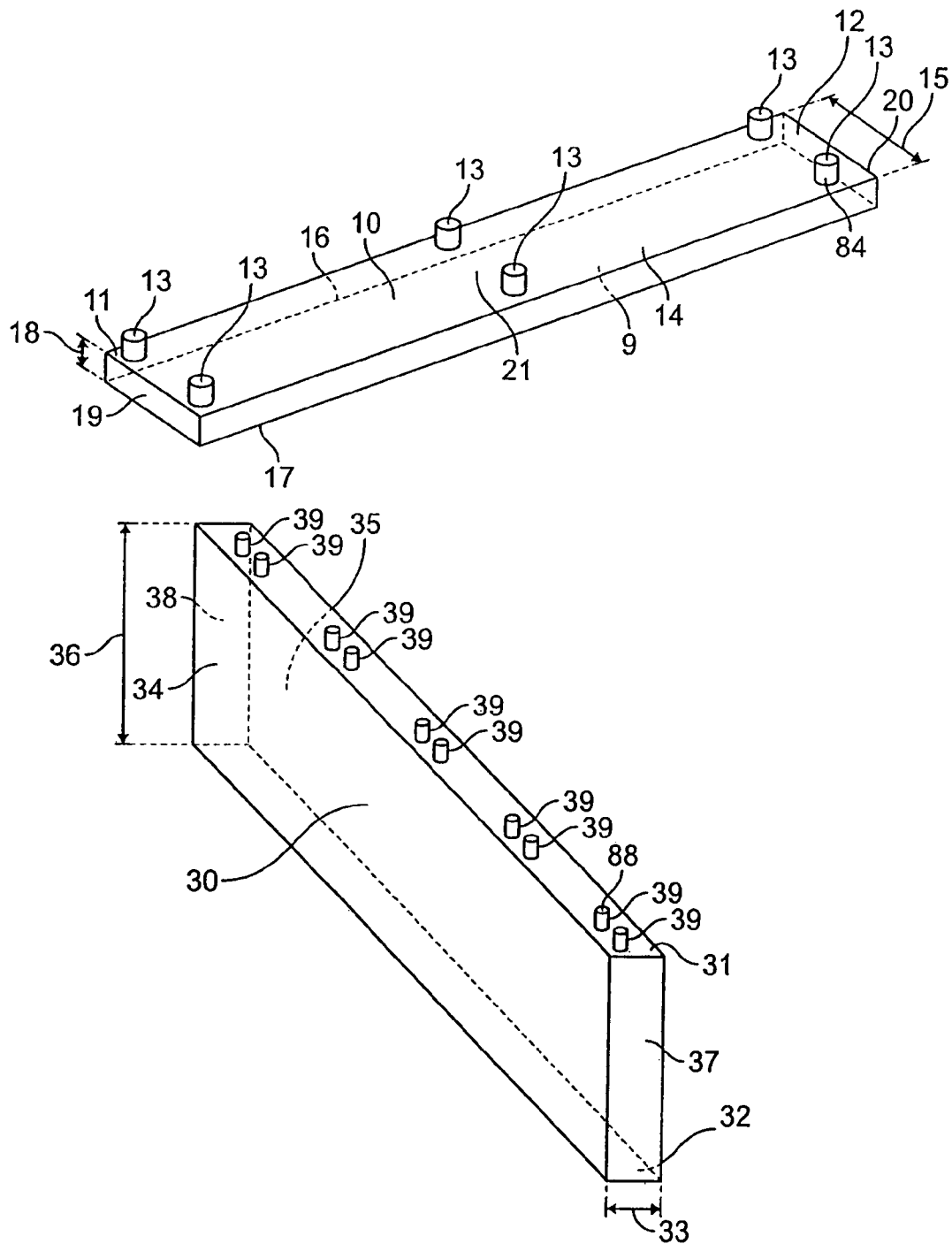
FIG. 1 is a perspective view of one embodiment of a deck board and stringer that may be used in the pallet of the subject invention.

While the present invention is susceptible of embodiments of various forms, there is shown in the drawings, and will hereinafter be described some exemplary and non-limiting embodiments, with the understanding that the present disclosure is to be considered an exemplification of the invention. It is not intended to limit the invention to the specific embodiments listed.

In general terms, one embodiment of the pallet comprises the combination of wooden dowels and adhesive to connect stringers and deck boards to form a pallet.

Referring to FIG. 1, a deck board 10 and a stringer 30 can be seen. The deck board 10 has a first end 11 and a second end 12. The deck board 10 comprises a first pair of opposing elongated longitudinal surfaces 9, 14 with a first width 15, a second pair of opposing elongated longitudinal surfaces 16, 17 with a second width 18 and a pair of end surfaces 19, 20. The first width 15 is greater than the second width 18. Both the first end 11 and the second end 12 have at least one opening 13. Preferably, the openings are in the same elongated surface 16, 17, 19, 20. More preferably, the openings 13 are in one of the first pair of elongated surfaces 16, 17. In one embodiment, both the first end 11 and the second end 12 have a plurality of openings 13. The openings 13 have an inner surface 84. Preferably, the deck board 10 is constructed of wood or like material. Along with first and second ends 11, 12 the deck board 10 can also have a middle section 21, wherein the middle section 21 has at least one opening 13 preferably in the same elongated surface 16, 17, 19, 20 as the openings 13 in the first and second ends 11, 12.

The stringer 30 comprises a first pair of opposing longitudinal mounting surfaces 31, 32 which have a first width 33. The stringer 30 further comprises a second pair of opposing longitudinal mounting surfaces 34, 35 which have a second width 36. The second width 36 is greater than the first width 33. The stringer 30 further comprises a pair of opposing end surfaces 37, 38. At least one of the longitudinal mounting surfaces 31, 32, 34, 35 has a plurality of bores 39 defined therein. The terms bore and opening are herein used synonymously. The different terms are used to more easily reference stringer (having bores) or deck board (having openings). The bores 39 have an inner surface 88. In one embodiment, the plurality of bores 39 are spaced substantially equally along a longitudinal mounting surface 31, 32, 34, 35. In another embodiment, opposing longitudinal surfaces, either 31, 32 or 34, 35, both have a plurality of bores 39. Preferably, the stringer 30 is made of wood or like material.

Figure 2:
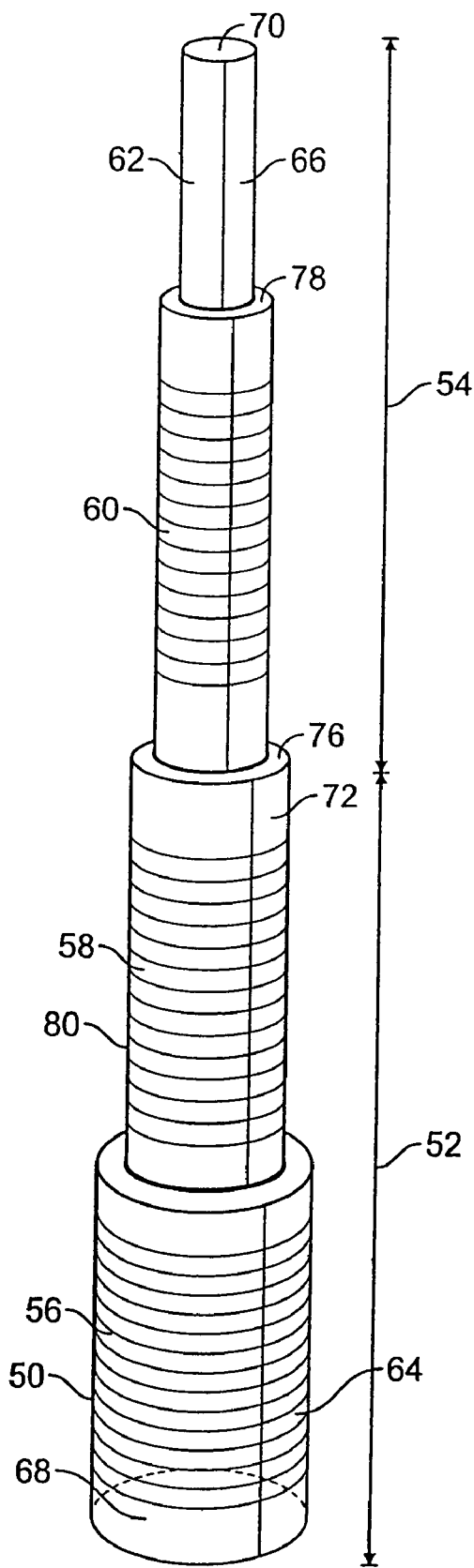
FIG. 2 is an elevated side view of one embodiment of a dowel used in the pallet of FIG. 1.

Referring to FIG. 2, one embodiment of a wooden dowel 50 can be seen. The dowel 50 comprises a first portion 52 and a second portion 54. The dowel may have a plurality of dowel sections, a first section 56, middle sections 58, 60, and last section 62. While in a preferred embodiment, the dowel 50 has two middle sections 58, 60 other embodiments may have no middle section, one middle section, or three or more middle sections. The first and last sections 56, 62 may have side walls 64, 66 and end walls 68, 70, respectively. Each of the middle sections 58, 60 may have side walls 72, 74 and step walls 76, 78, respectively. In a preferred embodiment, each of the sections 56, 58, 60, 62 are contiguous to another section 56, 58, 60, 62. The sidewalls 64, 66, 72, 74 define a cross-sectional size for their respective sections 56, 58, 60, 62. In a preferred embodiment, the cross-sectional size of the sidewalls 64, 66, 72, 74 decreases as one progresses from the first section 56 to the last section 62 in a number of steps. In another embodiment, the cross-sectional size of the sidewalls is greatest in a middle section (not shown). The cross-sectional size of the sidewalls 64, 66, 72, 74 may be any suitable size. The length of each individual dowel section 56, 58, 60, 62 may vary considerably. In one embodiment, the dowel section 656, 58, 60, 62 with the smallest cross-sectional size is as long or longer than the length of any of the other dowel sections. The dowel 50 may have some sections, e.g., 58, 60 or all sections 56, 58, 60, 62 that have grooves 80. The dowel 50 may have other configurations, such as, the dowel shown and described in U.S. Pat. No. 6,267,527, which is hereby incorporated by reference.

Figure 3:
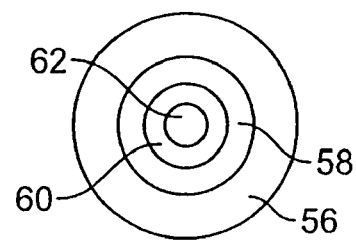
FIG. 3 is an end view of the embodiment of the dowel depicted in FIG. 2.

As shown in FIG. 3, an embodiment is depicted having dowel sections 56, 58, 60, 62 having a circular configuration. Other embodiments of the dowel 50 may be constructed so that each dowel section has a substantially square, triangular, or other cross-section. Further embodiments may mix and match square sections with triangular sections, or try other combinations. It is preferred that the dowel 50 be constructed from a single integral piece of wood. The dowel 50 may be constructed of different pieces of wood that are functionally attached to form the dowel 50. The dowel 50 is preferably made substantially of birch, but may also be made of red oak, cherry, ash, beech, or other suitable preferably hardwoods.

Figure 4:
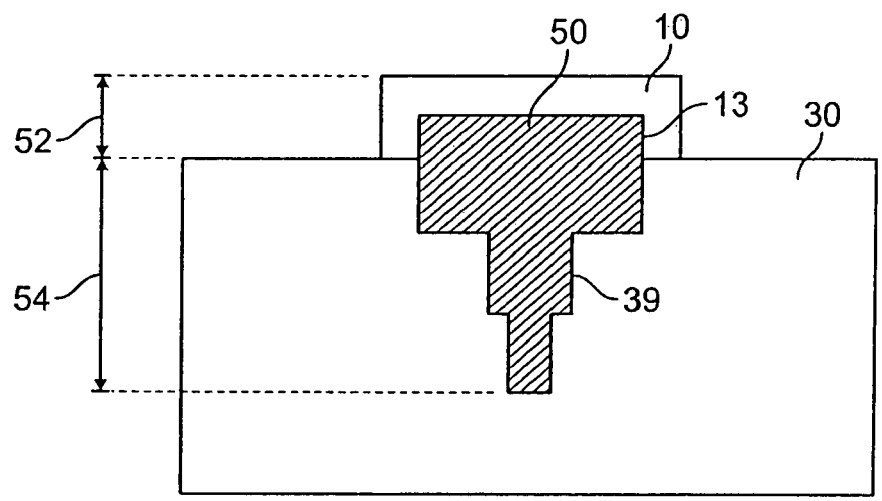
FIG. 4 is a side view of one embodiment of a dowel utilized in the subject invention to connect a stringer to a deck board.

As shown in FIG. 4, the dowel 50 connects the stringer 30 and the deck board 10. The opening 13 of the deck board 10 is configured to receive either the first or second portion 52, 54 of the dowel 50. The opening 13 is preferably sized so that it is slightly smaller than the dowel portion 52, 54 that it is configured to receive. The dowel 50 may fit snugly into the opening 13. Preferably, the dowel 50 and the opening 13 form a friction fit. In a preferred embodiment, the dowel 50 can be partially inserted into the opening 13 by hand. Because of the stepped nature of the dowel 50, the dowel 50 can be partially inserted into the opening 13 with minimal force. The partially inserted dowel 50 in the opening 13 of the deck board 10 is aligned with a selected bore 39 of the stringer 30. The selected bore 39 can configured to receive the portion of the dowel 50, either first or second 52, 54, that the opening 13 of the deck board 10 has not received. This receipt of the dowel shank 52, 54 in a cinching fashion is achieved by machining the bore 39 to a smaller cross section area in the stringer or second wood piece. Thus, the bore 39 cinches or grabs the dowel portions 52,54. While the bore 39 is receiving the dowel in a cinching fashion, the bore or opening in the first piece of wood or deck board is machined so that the opening 13 in deck board 10 is the same size or larger than dowel 50 cross sectional area. This means that the dowel 50 fits into the opening 39 in a cinching and grabbing fashion caused by the compression of the dowel surface by the surrounding wood on the surface of the pilot hole for a tight grip caused by the ratio of the dowel cross sectional area to the pilot hole cross sectional area being greater than one while the opening 13 is simply a snug, taut, or firm fit to the dowel and does not cinch the dowel caused by the ratio of the dowel cross sectional area to the pilot hole cross sectional area being less than or equal to one The pallet components are held together by cross sectional differences in the component openings and the respective bores with the dowel cross sections, whereby the openings 13 are equal to or very slightly larger than the dowel head or top (first section 56) and less than the diameter of dowel 50 in the middle and last sections 58.60, and 62. Alternatively the second stage down from the top of dowel 50 can have a cross sectional area that is larger than the cross sectional area of the section stage of the pilot hole in the deck board 10 or first piece of wood such that the cap portion of dowel 50 has a cross sectional area equal to or less than the cross sectional area of the cap portion of dowel 50 and greater than the cross sectional area of the second section of dowel 50 in the first piece of wood 10. This provides for cinching of the dowel in the second piece of wood to be joined and cinching of the dowel in the lower portion of the first piece of wood to be joined while allowing a snug fit in the top cap portion of the dowel in hole 13 of board 10. The forgoing allows for the dowel to act like a nail in pulling the first piece of wood tightly to the second piece of wood. Again, because of the stepped nature of the dowel 50, the dowel can be partially inserted into the bore 39 with minimal effort. Through the ability to be partially inserted with minimal force, the dowel 50 provides proper alignment of the opening 13 with the bore 39. The dowel 50 can be substantially or fully inserted into the opening 13 and bore 39 through the use of a suitable pounding device (not shown), such as a hammer or mallet, or through manual strength. The dowel 50 may fit snugly into the selected opening 13 and bore 39. Preferably, the dowel 50 and the opening 13 and bore 39 form a friction fit. Preferably, adhesive (not shown) is disposed between the abutting parts of the dowel 50, stringer 30 and deck board 10.

Figure 5:
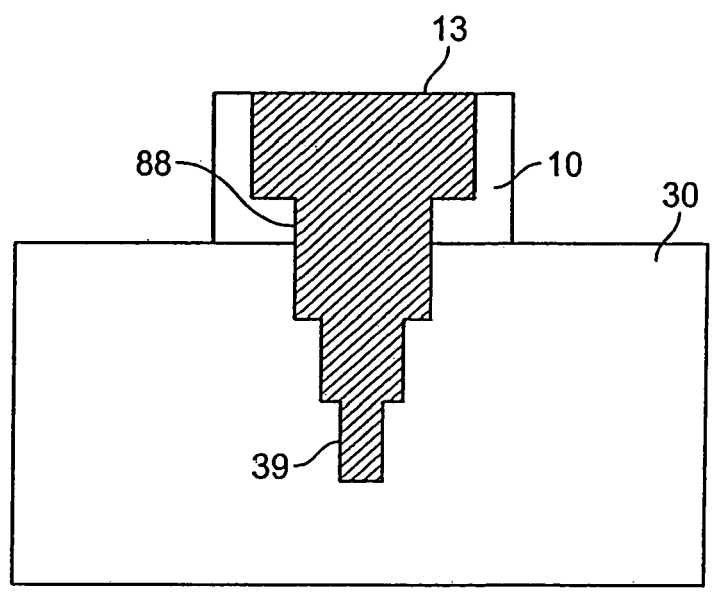
FIG. 5 is a side view of another embodiment of a dowel utilized in the subject invention to connect a stringer to a deck board.

Referring now to FIG. 5, a second embodiment of the connection between a selected stringer 30 and a selected deck board 10 can be seen. In this embodiment, the opening 13 is such that it defines a hole 82 through the deck board 10. In other embodiments, the bore 39 defines a hole 82 through the stringer 30, or both the bore 39 and the opening 13 define holes 82 in the stringer 30 and deck board 10, respectively. An advantage of this embodiment is that it allows the dowel 50 to be more easily inserted into both the deck board 10 and stringer 30 almost simultaneously. This embodiment also allows for one-step desired alignment of the opening 13 with the bore 39. In this embodiment, the opening 13 and bore 39 can be created at the same time using a properly shaped drill (not shown) or other suitable device. The drill bit (not shown) used with a drill may have many configurations, such as the drill bit shown and described in U.S. Pat. No. 6,267,527, which is hereby incorporated by reference. The deck board 10 can be placed in a predetermined alignment with the stringer 30. An operator can then drill a hole 82 through the deck board 10, creating the opening 13, and then continue to drill into the stringer 30 to create the corresponding bore 39.

Figure 6:
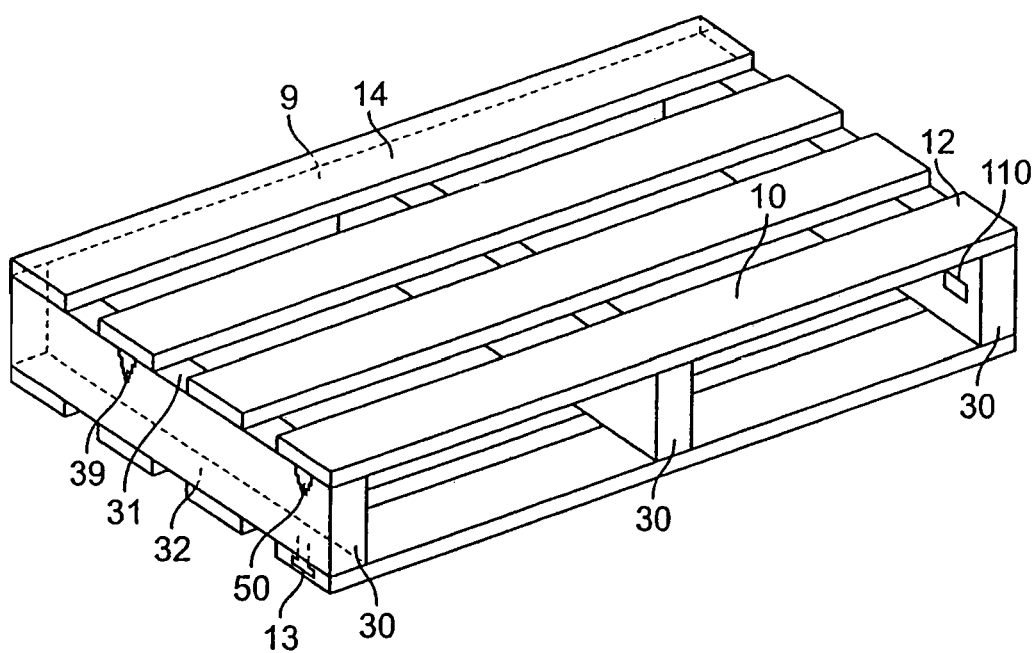
FIG. 6 is a perspective view of one embodiment of the subject invention showing a pallet comprising stringers, deck boards and dowels.

Referring now to FIG. 6, an embodiment of the pallet is depicted as having three stringers 30 orientated in substantially the same plane in a parallel relationship. Many other pallet configurations may be used including, e.g., the stringer design, the block design, skids, stevedore type double wing, plywood panel deck stringer, nine block four-way entry pallet, single wing pallet with optional chamber on bottom boards, or the reversible stringer pallet. This list is given as an example of some types of pallets, and is not intended to be exhaustive. One of skill in the art would recognize that a wide variety of pallet formations can be contemplated and would fall within the scope of the invention.

As shown in FIG. 6, one embodiment may have first, second, and third stringers 30 arranged parallel to each other. The second stringer 30 is spaced a substantially equal space from the first and third stringers 30, respectively. The distance between the first and third stringer 30 is substantially equal to the length of a pre-selected deck board 10. Each of the first pair of opposing longitudinal mounting surfaces 31, 32 has a plurality of bores 39 (some not shown) defined therein The embodiment may have a plurality of deck boards 10 arranged parallel to each other and transverse to the stringers 30. Preferably, one of the first pair of opposing elongated longitudinal surfaces 9, 14 of each deck board 10 has a plurality of openings 13 (some not shown) defined therein. The deck boards 10 are arranged such that the openings 13 defined in the first end 11, second end 12 and middle section 21 are aligned with the bores 39 defined in the stringers 30. A plurality of dowels 50 are fit into the openings 13 and aligned bores 39 to connect the stringers 30 to the deck boards 10. One set of deck boards 10 are connected opposing longitudinal mounting surface 31 while a second set of deck boards 10 are connected to opposing longitudinal mounting surface 32.

Figure 7:
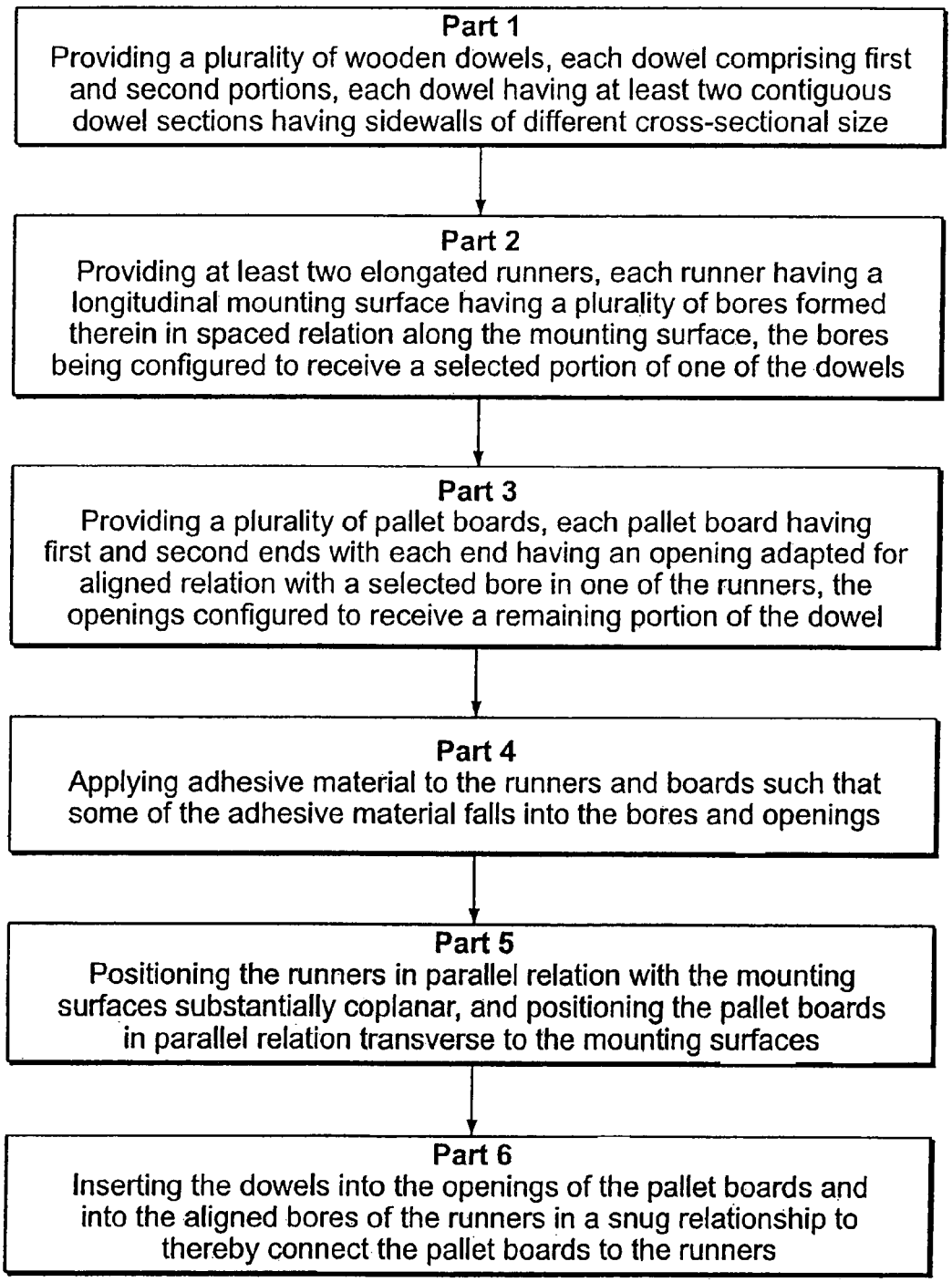
FIG. 7 sets forth the steps in one embodiment of a method for assembling a pallet according to the subject invention.

FIG. 7 sets forth the steps of a preferred method for forming a pallet. It should be noted that FIG. 7 gives numbers to Parts of the method for ease of reference only. The invention can be performed in an order different than that provided. The reference numerals, e.g. dowel 50, provided below refer to FIGS. 1-6.

Part 1 of FIG. 7 recites the step of providing a plurality of wooden dowels 50. Each of the dowels 50 comprises first and second portions 52, 54 and has at least two contiguous dowel sections 56, 62 having sidewalls 64, 66 of different cross-sectional size. The dowels 50 may be of the type shown in FIGS. 2-6 and described above.

Part 2 recites providing of at least two elongated stringers 30. Each stringer 30 has a longitudinal mounting surface 31 having a plurality of bores 39 formed therein in spaced relation along the mounting surface 31. The bores 39 are configured to receive a selected portion 52, 54 of one of the dowels 50.

Part 3 describes the step of the providing of a plurality of deck boards 10. Each of the deck boards 10 has first and second ends 11, 12 with each end having an opening 13 adapted for aligned relation with a selected bore 39 in one of the stringers 30. The openings 13 are configured to receive a remaining portion 52 or 54 of the dowel 50. The bores 39 and openings 13 can be configured with the use of a drill (not shown) with attendant drill bit (not shown). The drill bit may have many configurations, such as, e.g., the drill bit shown and described in U.S. Pat. No. 6,267,527, which is hereby incorporated by reference. Preferably, the stringers 30 and deck boards 10 provided are comprised of a dry wood. The method can further comprise providing an RFID device (shown as 110 in FIGS. 6 and 8) to be attached to the pallet.

Part 4 recites the application of adhesive material (not shown) to the stringers 30 and deck boards 10 such that some of the adhesive material is disposed in the bores 39 and openings 13. The adhesive material may be applied to the surfaces 31, 32, 34, 35, 13, 14, 16, 17, of the stringers 30, deck boards 10 or side walls 64, 66, 72, 74 of the dowels 50 to strengthen or augment the connection. The adhesive material is preferably PVA, but can be any material that would adequately connect the parts of the pallet together, such as, e.g., elastomers, hot melts, urethane, epoxy, PRF, or urethane/isocyanate. Preferably, during the construction of a pallet, the adhesive is applied to the stringers 30 and deck boards 10 such that some of the adhesive is disposed in the bores 39 and openings 13 prior to the insertion of the dowels 50. The adhesive material may also be applied to the side walls 64, 66, 72, 74 of the dowel 50. In a preferred embodiment, the adhesive applied to the dowel 50 is thinned to allow for more ready insertion and connection. As the dowel is inserted into the bore or opening 13, the adhesive material may be at partly scraped from the side walls 64, 66, 72, 74 to accumulate on the end wall 70 and step walls 76, 78.

Part 5 recites the positioning of the stringers 30 in parallel relation with the mounting surfaces 31, 32 of different stringers 30 in substantially coplanar relation, and positioning the deck boards 10 in parallel relation transverse to the mounting surfaces 31, 32.

Part 6 recites the insertion of the dowels 50 into the openings 13 of the deck boards 10 and into the aligned bores 39 of the stringers 30 in a snug relationship to thereby connect the deck boards 10 to the stringers 30. The stepped configuration of the dowel 50 provides easier alignment of the dowel 50 with the opening 13 and bore 39 during the insertion process. Further, significant pressure need be only applied to the dowel 50 during, for example, approximately the last 20 percent of the insertion distance. A pounding device (not shown) may be used to insert the dowels. This device may be a hammer, mallet, or other suitable instrument. Preferably, the dowels 50 fit snugly into the openings 13 and bores 39. Most preferably, the dowels 50 form a friction fit with the inner surface 84, 88 of the opening 13 or bore 39. The snug or friction fit connects the deck boards 10 to the stringer 30. Using a dowel 50 with grooves 80 yields a connection that is stronger. One benefit of the dowel 50 is that it acts as an internal clamping mechanism that holds the pallet together while the adhesive sets or cures. This benefit provides needing flexibility to the manufacturing process, allowing more ready manufacture of pallets. For example, the use of the dowels 50 can eliminate the need for external clamps or other devices (not shown) to maintain connection of the deck boards 10 to the stringers 30 while the adhesive cures. The manufacturer can thus avoid the costs of these external clamps as well as the time, effort, and floor space needed to utilize them. A second benefit of the use of the dowel 50 is that it can allow for the use of a wide variety of adhesive materials. A pallet manufacturing operations using adhesives may have the capability of manufacturing a number of pallets per unit time. However, the need for space to allow for the adhesive in the pallets to set or cure is great. Typically, these operations will thus prefer adhesives with very short set or cure times, even though these adhesives are not optimal on a cost or performance basis. The use of the dowel 50 to connect the runners 10 to the stringers 30 allow for the practical use of adhesives with longer cure times because the pallet can be handled and used while the adhesive is setting or curing. It also allows for the use of adhesives that are approved for use in the transport of food.

Figure 8:
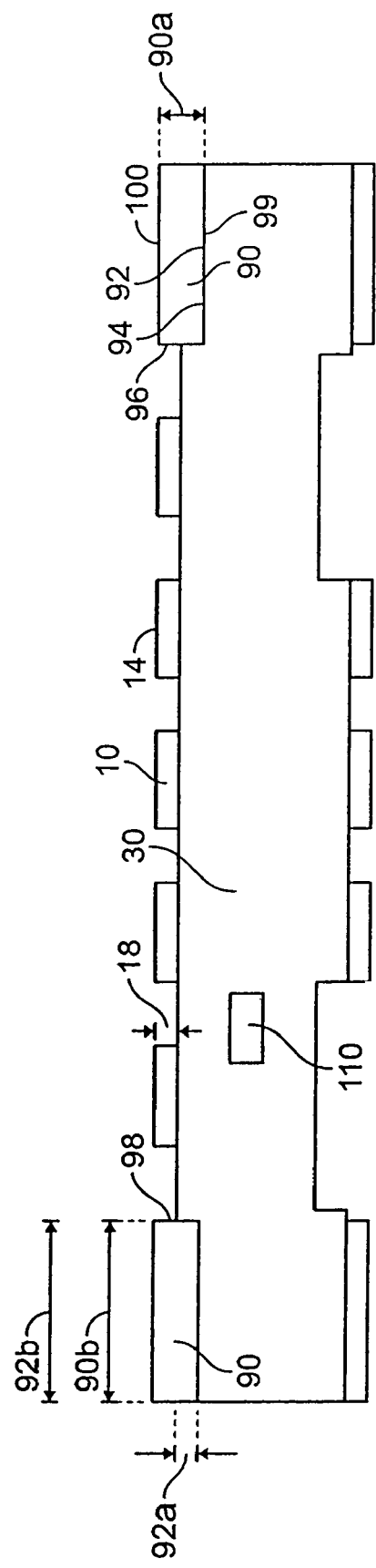
FIG. 8 is a side view of another embodiment of the subject invention showing a pallet with a notched stringer.

Referring now to FIG. 8, a side view of a preferred embodiment of a pallet is shown. FIG. 8 shows a stringer 30, deck boards 10 and lead deck boards 90. The lead deck board 90 has a height 90*a* and a width 90*b* and opposing surfaces 99, 100. The stringer 30 comprises notches 92. The notches 92 can have a first surface 94 and a second surface 96. The notches have a depth 92*a* and a width 92*b*. Preferably, the width 90*b* of the lead deck board 90 is substantially similar to the width 92*b* of the notches 92 so that the lead deck board 90 can be disposed in the notch 92. Preferably, the height 90*a* of the lead deck board 90 can be substantially similar to the sum of the width 18 of the deck board 10 and the depth 92*a* of the notch so that, when disposed in the notch 92, surface 100 can be substantially planar to surface 14 of the deck boards 10. In this embodiment, the lead deck board 90 is able to withstand a greater shearing force because the connection between the lead deck board 90 and stringer 30 receives lateral support from the second surface 96 of the stringer 30. The lead deck board 90 can be connected to the stringer 30 with wooden dowels 50 and adhesive.

In another embodiment, the notches 92 can have an angled second surface 96 (angle not shown). Preferably, a corresponding surface 98 of the lead deck board 90 is angled complimentary to the angled second surface 96 to form, e.g., a dovetail configuration (not shown). Preferably, the deck boards and lead deck boards are connected to the stringer 30 using a wooden dowel 50 and adhesive, as described hereinabove.

In a preferred embodiment, the pallet described herein consists essentially of wood and adhesive. In the most preferred embodiment, the pallet consists of wood and adhesive. The use of a wooden dowel 50 and wooden stringers 30 and deck boards 10, along with adhesive, can, through construction, create a pallet that exceeds industry requirements for static strength, stiffness, and resistance to rough handling.

Further, the pallet described herein can be substantially lighter than standard pallets that employ nails or other metal fasteners. First, the use of wooden dowels inserted into bores or openings instead of nails creates less weight. The weight of the dowel 50 being inserted is offset by the amount of wood drilled out of the deck boards 10 and stringers 30. With the use of nails, there is no offset. With the use of a large number of nails in typical pallets (sometimes over one hundred for a used pallet), this weight difference can become substantial. Second, the pallet described herein can be made with kiln dried wood, which is lighter than wet or green wood. Typical pallets are made of wet or green wood because hammering in nails in dry wood can cause damage to the wood, such as checking, and result in a damaged or weakened pallet. Through the use of the dowel 50, the pallet described herein can be constructed of wood that is kiln dried. Preferably, the wood is less than 15% moisture and more preferably between 9 and 12% moisture. The pallet described herein can be substantially lighter than typical patents, making them less likely to cause injury to workers during transport, and also yielding substantial savings in fuel economy during transport.

It is believed that the pallet described herein can be constructed so that it meets industry requirements for a rated load of 2800-pounds that is less than sixty pounds. Preferably, such a pallet will be between fifty three and fifty eight pounds. More preferably, such a patent will be less than fifty three pounds. In contrast, the typical wooden pallet can weigh from seventy to eighty pounds.

The construction of a pallet of essentially all kiln dried wood and adhesive creates further advantages. A significant advantage is that the pallet is less likely to interfere with RFID. As seen in FIGS. 6 and 8, an RFID device 110 can be attached to the pallet. Preferably, the RFID device 110 is attached to an inside surface 34 or 35 of the middle stringer 30 or one of the outside stringers 30. A warehouse (not shown) can have an RFID reader (not shown) near a dock door. When the pallet described herein, with the attached RFID device 110, enters the warehouse, the RFID reader will can read the RFID device 110. RFID readers can have difficulty reading RFID devices which are near liquid, which absorbs RF signals. The pallet described herein can be constructed of dried wood, lessening the amount of RF signal absorption and potentially allowing for higher read rate accuracy. Further, the pallet described herein is preferably constructed without metal. Metal can prevent RF readers from working properly. The pallet described therein is therefore likely to yield higher read rate accuracy.

The preferred lack of metal also allows for the pallet to be subjected to microwave sterilization. This potentially results in a pallet that does not, for example, transport alien organisms or animals from one region to another.

The present invention is not limited to their particular details of the method depicted, and other modifications and applications are contemplated. Certain other changes may be made in the above-described method without departing from the true spirit and scope of the invention herein involved. For example, the present method may be utilized with other styles of pallets, which have different formations of stringers, panel boards, or like members. It is intended, therefore, that the subject matter in the above depiction shall be interpreted as illustrative and not in a limiting sense.

What is claimed is:

1. A method for assembling a pallet comprising:
   providing a plurality of wooden dowels, each dowel comprising a top surface and first and second lower portions, each dowel having at least two contiguous dowel cylindrical sections having sidewalls of different cross-sectional size;
   providing a plurality of elongated wooden pallet stringers, each stringer having at least one mounting surface and a top surface;
   providing a plurality of deck boards;
   positioning the deck boards in spaced parallel arrangement;
   positioning the stringers perpendicular to said deck boards, spaced from one another; and
   wherein each stringer is connected to at least two of said plurality of deck boards by providing pilot holes that extend through each deck board and into each stringer at an angle substantially perpendicular to the mounting surfaces, wherein the pilot holes having at least an upper pilot hole and a lower pilot hole section having decreasing cross-sectional size;
   applying adhesive material to the mounting surfaces of the pallet stringers;
   applying adhesive material to the pilot holes or dowels such that adhesive material is ultimately disposed in the pilot holes;
   inserting the dowels through the deck boards into the pilot holes of the stringers so that the pilot holes cinch the dowels at a lower portion with a ratio between the lower pilot hole cross sectional area and the dowel cross sectional area less than one and there is a snug fit at a top portion of the dowel with a cross sectional area of the upper pilot hole to be equal to or greater than the cross sectional area of the dowel.

2. The method of claim 1, wherein the adhesive cures in less than about five minutes under normal conditions.

3. The method of claim 1 wherein the adhesive material is applied so that it is•disposed on substantially all of the mounting surfaces of the pallet stringers.

4. The method of claim 1, further comprising attaching an RFID device to the pallet.

5. The method of claim 1, further comprising creating the pilot hole with a drill.

6. The method of claim 1 wherein the pallet stringers are comprised of dry wood having less than about 15% moisture by weight.

7. The method of claim 1 wherein the pallet can hold a load of 2800-pounds and weighs less than 60 pounds.

8. The method of claim 1 wherein the pallet weighs less than 53 pounds.

9. The method of claim 1 wherein the dowels have at least three dowel sections of successively decreasing cross-sectional sizes and the pilot holes have at least three pilot hole sections of successively decreasing cross-section size.

10. The method of claim 1 wherein the pallet consists essentially of wood and adhesive.

11. The method of claim 4 wherein the pallet consists essentially of wood, adhesive, and an RFID device.

12. The method of claim 1 wherein the dowels form a friction fit in the pilot holes.

13. The method of claim 10 wherein the pallet is assembled without the use of external clamps.

14. A substantially wooden pallet comprising:
   a plurality of wooden pallet stringers and deck boards positioned to form a pallet, the deck boards being spaced and parallel, and the stringers being spaced and parallel to one another, and transverse to and adjacent the deck boards, the deck boards having a mounting surface and a top surface;
   wherein each stringer is connected to at least two of said plurality of deck boards by deck boards having pilot holes extending substantially perpendicular to the mounting surface through the deck boards and into adjacent stringers, the pilot holes being completely through said deck boards and said stringer having at least two contiguous pilot hole sections with diameters of decreasing cross-sectional size;
   adhesive disposed on the mounting surfaces and in the pilot holes; and; a plurality of wooden dowels comprising at least upper and lower dowel sections having sidewalls of different cross-sectional size and a top surface, wherein the wooden dowels are disposed in the pilot holes such that the top surface of the pallet deck boards and the top surface of the dowels are substantially co-planar, wherein the dowels connect the deck boards and stringers through a cinching action on the lower dowel section caused by a pilot hole cross sectional area to dowel cross sectional area ratio less than one and a pilot hole cross sectional area to dowel cross sectional area ratio one or greater such that no cinching takes place or a snug fit on the upper dowel section.

15. A pallet as defined in claim 14 wherein the pallet weighs less than 60 pounds and can carry a load of 2800 pounds.

16. A pallet as defined in claim 14 wherein the dowel sidewalls are at least partially grooved.

17. A pallet as defined in claim 14 wherein the dowels having at least three contiguous dowel sections of successively decreasing cross-sectional size and the pilot holes having at least three contiguous pilot hole sections of successively decreasing cross-sectional diameter.

18. A pallet as defined in claim 17 wherein the at least three contiguous dowel sections are cylindrical.

19. A pallet as defined in claim 14 wherein the dowel sidewalls are at least partially ribbed.

20. A pallet as defined in claim 14, further comprising an RFID device attached to the pallet.

21. A pallet as defined in claim 14, wherein the pallet components are comprised of dry wood having less than about 15% moisture by weight during construction.

22. A pallet comprising:
a plurality of deck boards and stringers, each deck board including a longitudinal mounting surface having a plurality of vertical bores formed therethrough;
a plurality of stringers having a plurality of substantially vertical openings in the mounting surface each of said openings corresponding to a vertical bore;
said deck boards being spaced and parallel;
said stringers being spaced and transverse to said deck boards;
said deck boards being adjacent said stringers;
wherein each stringer is connected to at least two of said plurality of deck boards by a plurality of fasteners consisting of wooden dowels, each dowel having upper and lower portions of different cross sectional size, wherein the upper portions are inserted in through the vertical bores of the deck boards through to the plurality of respective vertical openings such that the deck boards and stringers are connected together in a predetermined orientation to form a pallet, wherein each of the wooden dowels comprises at least two contiguous dowel sections having different cross-sectional size so that the first pallet vertical bores each has a cross sectional area to dowel cross sectional area ratio less than one in the lower portion of the dowel and the cross sectional area of the bores to dowel cross sectional area ratio is one or greater in the cross sections of the vertical openings of the first pallet component in the upper portion of the dowel.

* * * * *